US011886267B2

(12) United States Patent
Ghoshal et al.

(10) Patent No.: US 11,886,267 B2
(45) Date of Patent: Jan. 30, 2024

(54) USER PRESENCE DETECTION SYSTEMS FOR CONTROL OF ELECTRONIC DEVICES

(71) Applicant: ADVANCED TELESENSORS, INC., Austin, TX (US)

(72) Inventors: Sajol Ghoshal, Austin, TX (US); David Kramer, Cedar Park, TX (US); Jaime Martinez, Austin, TX (US)

(73) Assignee: Advanced Telesensors, Inc., Austin, TX (US)

( * ) Notice: Subject to any disclaimer, the term of this patent is extended or adjusted under 35 U.S.C. 154(b) by 80 days.

(21) Appl. No.: 17/421,376

(22) PCT Filed: Jan. 8, 2020

(86) PCT No.: PCT/US2020/012708
§ 371 (c)(1),
(2) Date: Jul. 7, 2021

(87) PCT Pub. No.: WO2020/146476
PCT Pub. Date: Jul. 16, 2020

(65) Prior Publication Data
US 2022/0083120 A1 Mar. 17, 2022

Related U.S. Application Data

(60) Provisional application No. 62/789,783, filed on Jan. 8, 2019.

(51) Int. Cl.
*G06F 1/3231* (2019.01)
*G06V 40/10* (2022.01)
(Continued)

(52) U.S. Cl.
CPC ............ *G06F 1/3231* (2013.01); *G01S 7/412* (2013.01); *G01S 13/56* (2013.01); *G06F 3/011* (2013.01);
(Continued)

(58) Field of Classification Search
CPC ....... G06F 1/3231; G06F 3/011; G06V 40/10; G01S 7/412; G01S 13/56
See application file for complete search history.

(56) References Cited

U.S. PATENT DOCUMENTS 3,993,995 A 11/1976 Kaplan et al.
5,760,687 A 6/1998 Cousy
(Continued)

FOREIGN PATENT DOCUMENTS

KR 1020160022163 A 2/2016

OTHER PUBLICATIONS

Boric-Lubecke, "Wireless Biomedical Sensors," Lucent Technologies-Bell Labs Innovations, 27 pages.
(Continued)

*Primary Examiner* — Abbas I Abdulselam
(74) *Attorney, Agent, or Firm* — Withrow & Terranova, PLLC; Vincent K. Gustafson (57) ABSTRACT

An electronic device incorporating a liquid crystal display (LCD) screen comprises at least one at least one radio frequency (RF) antenna mounted behind a LCD panel of the LCD screen, and a processor. The RF antenna includes a directional transmit RF antenna that transmits an RF signal through the LCD panel to impinge on a human user, and includes a receive antenna configured to receive a RF signal reflected from tissue of the human user. The processor processes the reflected RF signal to generate a processed signal indicative of presence or absence of the human user, and responsive to the processed signal, controls an operating mode of the electronic device and/or enables control of the device by the human user.

20 Claims, 5 Drawing Sheets

(51) Int. Cl.
*G01S 7/41* (2006.01)
*G01S 13/56* (2006.01)
*G06F 3/01* (2006.01)
*H01Q 21/06* (2006.01)
*G06F 21/31* (2013.01)
*H01Q 1/22* (2006.01)

(52) U.S. Cl.
CPC .............. *G06V 40/10* (2022.01); *H01Q 21/06* (2013.01); *G06F 21/31* (2013.01); *G06V 40/15* (2022.01); *H01Q 1/22* (2013.01)

(56) References Cited

U.S. PATENT DOCUMENTS

| | | | |
|---|---|---|---|
| 6,011,477 | A | 1/2000 | Teodorescu et al. |
| 7,272,431 | B2 | 9/2007 | McGrath |
| 7,811,234 | B2 | 10/2010 | McGrath |
| 9,492,099 | B2 * | 11/2016 | Gamble ................ A61B 5/0507 |
| 2006/0256766 | A1 * | 11/2006 | Baldor .................... H04L 45/60 |
| | | | 370/347 |
| 2007/0060827 | A1 | 3/2007 | Kobayashi et al. |
| 2008/0071181 | A1 | 3/2008 | Stabler et al. |
| 2008/0119716 | A1 | 5/2008 | Boric-Lubecke et al. |
| 2009/0143692 | A1 | 6/2009 | Brockway et al. |
| 2009/0156945 | A1 | 6/2009 | Baruch |
| 2010/0152600 | A1 | 6/2010 | Droitcour et al. |
| 2012/0123232 | A1 | 5/2012 | Najarian et al. |
| 2014/0370929 | A1 * | 12/2014 | Khawand ............. H04B 1/3838 |
| | | | 455/522 |
| 2017/0055912 | A1 | 3/2017 | Gamble et al. |
| 2017/0336505 | A1 * | 11/2017 | Driscoll ................ G01S 13/867 |

OTHER PUBLICATIONS

Nagae, Daisuke et al., "Measurement of heart rate variability and stress evaluation by using microwave reflectometric vital signal sensing," Review of Scientific Instruments, vol. 81, No. 9, Sep. 13, 2010, American Institute of Physics, 10 pages.

Perry, Christopher M. et al., "Non-Contact Vital Sign Monitoring via Ultra Wideband Radar, Infrared Video, and Remote Photoplethysmography: Viable Options for Space Exploration Missions," National Aeronautics and Space Administration, May 2011, Johnson Space Center, 15 pages.

Scalise, Lorenzo, "Non Contact Heart Monitoring," Advances in Electrocardiograms—Methods and Analysis, Chapter 4, Millis, Richard, M., (Ed.) Jan. 25, 2012, InTech, pp. 81-106.

Notification of Transmittal of the International Search Report and Written Opinion (Form PCT/ISA/220), International Search Report (Form PCT/ISA/210), and Written Opinion (Form PCT/ISA/237) for International Application No. PCT/US2020/012708 dated Mar. 20, 2020, 11 pages.

* cited by examiner

FIG. 6

USER PRESENCE DETECTION SYSTEMS FOR CONTROL OF ELECTRONIC DEVICES

CROSS-REFERENCE TO RELATED APPLICATIONS

This application is a 35 U.S.C. § 371 national phase filing of International Application No. PCT/US2020/012708 filed on Jan. 8, 2020, and claims the benefit of U.S. Provisional Patent Application No. 62/789,783 filed on Jan. 8, 2019, wherein the entire disclosures of the foregoing applications are hereby incorporated by reference herein.

TECHNICAL FIELD

Subject matter herein relates to detection of one or more users to control operation of electronic devices, as may be useful to promote power saving and/or prevent unauthorized access to such devices.

BACKGROUND

Current electronic devices such as personal computers, laptops, tablets, medical equipment, industrial equipment, etc., include a variety of user input/output interfaces and a visual display to convey pertinent information to the user. Such devices can entail relatively high power consumption when functioning. The displays of such devices typically contain an active light source which transmit light through various layers of optical processing that illuminate a set of pixels through polarizers and color filters. Current generation of displays are based on LCD technology with either cold cathode fluorescent lamp (CCFL), external electrode fluorescent lamp (EEFL), hot cathode fluorescent lamp (HCFL), flat fluorescent lamp (FFL), or light emitting diode (LED) backlights. These monitors consume between 20 and 40W of power when active. If the system is working on background processes, the display is not needed. The other processing components of the system when active also consume operating power which could be as high as 300W.

Energy saving efforts such as Energy Star 7.0, July 2016 mandate maximum power consumption allowed during certain operational modes such as active, standby, and off in order to achieve the relevant certification, and be deemed energy efficient. What is omitted in these energy savings standards is the policies and rules for transition from active mode to standby mode, and any relevant metrics associated with it.

Energy savings algorithms that run on conventional electronic devices frequently utilize configurable timers to determine when a device should enter into a lower power state, sometimes called sleep state. If no user activity (e.g., user input) is detected within a configured time period, then a device will typically enter its prescribed power saving mode(s). Examples of power saving features that may be implemented include turning off any active display, suspending or closing software applications, reducing one or more processors to a standby mode, and the like. Once user activity is detected thereafter (e.g., via one or more input/output interfaces), the device will exit a sleep state and be active for use.

This timer-based approach to entering and exiting low power modes is inefficient and difficult to set to a usable value. Optimal power conservation is not achieved due to the time that an electronic device stays active after a user has moved away from it. Setting the timer to a very small value helps to mitigate the power efficiency problem, but creates user inefficiency issues as the electronic device takes several seconds to become active again, and users are frequently annoyed by losing device functionality.

Other power saving and user authentication technologies have been developed. Portable computing devices (e.g., smartphones, tablet computers, laptop computers, and the like) frequently include user access control schemes (e.g., "smart card" readers, password protection, or biometric sensing such as thumbprint scanning, facial recognition, etc.) as well as power saving features that will be triggered following a specified period in which no user inputs have been received.

Facial recognition typically the face of a user to be presented in a specific orientation to a camera. When a user's face is not properly positioned in close proximity to a camera, facial recognition may be ineffective. Additionally, as bezel sizes for portable computing devices continue to shrink, manufacturers of certain computing devices (e.g., laptop computers) may seek to relocate cameras to locations away from displays or eliminate cameras altogether. Thumbprint scanners may be inconvenient for users to operate and/or exhibit inconsistent operation depending on factors such as hydration of a user's skin.

U.S. Pat. No. 6,650,322 discloses a power control device for a computer that uses at least one thermal sensor to determine presence of a user based on an amount of temperature fluctuation (e.g., due to user respiration proximate to the computer) occurring in a specified time period.

U.S. Pat. No. 6,665,805 discloses a power control device for a computer that utilizes a camera to detect presence of a user, and that manages power consumption of the computer based on processing of image data to determine whether a user is proximate to the computer.

U.S. Pat. No. 9,152,209 discloses an apparatus for controlling an operating mode (e.g., a power saving mode) of a mobile terminal based on receipt of facial recognition data from a camera.

U.S. Pat. No. 9,330,246 discloses use of facial recognition technology such as infrared emission signatures or facial topography for continuous monitoring and comparison of facial recognition information to a database of predetermined recognition data to determine whether a specific authorized individual or individuals are present, and automatically logs the user or users out of the computer if the proper recognition data is not detected in a defined interval of time.

Need exists for improved systems and methods for detecting and/or authenticating human presence proximate to portable computing devices to address limitations of existing systems and methods in the art.

SUMMARY

The present disclosure relates in various aspects to devices and methods utilizing reflectometric detection of a human user in order to control an operating mode of an electronic device or enable control by the human user of the electronic device.

In one aspect, the disclosure relates to an electronic device comprising a liquid crystal display (LCD) screen, the electronic device comprising at least one radio frequency (RF) antenna mounted behind a LCD panel of the LCD screen, and at least one processor. The at least one RF antenna comprises a directional transmit RF antenna configured to transmit an RF signal forward through the LCD panel to impinge on tissue of a human user, and the at least one RF antenna comprises a receive antenna configured to receive a reflected RF signal that comprises a reflection of the RF signal impinged on tissue of the human user. The at least one processor is configured to process the reflected RF signal to generate a processed signal indicative of presence or absence of the human user, and, responsive to the processed signal, control an operating mode of the electronic device or enable control by the human user of the electronic device.

In certain embodiments, the RF signal comprises a pulsed RF signal.

In certain embodiments, the RF signal comprises a swept frequency RF signal.

In certain embodiments, the RF signal comprises a static RF signal.

In certain embodiments, functionality of the receive antenna is provided by the directional transmit RF antenna.

In certain embodiments, the at least one RF antenna comprises an RF antenna array.

In certain embodiments, the directional transmit RF antenna comprises a first RF antenna array, and the receive antenna comprises a second RF antenna array.

In certain embodiments, the RF signal is in a microwave frequency band.

In certain embodiments, processing of the reflected RF signal comprises detection of gross motion of the human user as an indicator of presence of the human user.

In certain embodiments, processing of the reflected RF signal comprises detection of respiration rate of the human user as an indicator of presence of the human user.

In certain embodiments, processing of the reflected RF signal comprises detection of a cardiac signal of the human user as an indicator of presence of the human user.

In certain embodiments, processing of the reflected RF signal comprises detection of respiration rate, blood pressure, and/or a cardiac signal, without identification of gross motion of the human user, as an indicator of presence of the human user.

In certain embodiments, the at least one processor is configured to dynamically adjust sensitivity in the processing of the reflected RF signal to account for attenuation of the reflected RF signal attributable to transmission losses through the LCD panel and path loss to the human user.

In certain embodiments, the at least one processor is configured to control an operating mode of the electronic device by initiating a low power consumption mode or shutdown responsive to the processed signal when the processed signal indicates absence of the human user.

In certain embodiments, the at least one processor is configured to control an operating mode of the electronic device by initiating a normal power consumption mode or activation of the electronic device responsive to the processed signal when the processed signal indicates presence of the human user.

In certain embodiments, the processing of the RF signal comprises identifying a cardiac signal signature of the human user, and comparing the identified cardiac signal signature to at least one previously stored cardiac signal signature to authenticate the human user; and wherein at least one processor is configured to enable control by the human user of the electronic device when the processed signal indicates presence of the human user and the human user is authenticated.

In certain embodiments, an electronic device as disclosed herein may be embodied in a personal computer, laptop computer, or tablet computer.

In certain embodiments, an electronic device as disclosed herein may be embodied in medical equipment or industrial equipment.

In certain embodiments, any two or more aspects or embodiments or other features disclosed herein may be combined for additional advantage.

DETAILED DESCRIPTION

The present disclosure relates in various aspects to devices and methods utilizing reflectometric detection of a human user in order to control an operating mode of an electronic device or enable control by the human user of the electronic device. Such detection is contactless in nature, without requiring physical contact with a human user. In one aspect, the disclosure relates to an electronic device comprising a liquid crystal display (LCD) screen, the electronic device comprising at least one at least one radio frequency (RF) antenna mounted behind a LCD panel of the LCD screen, and at least one processor. The at least one RF antenna comprises a directional transmit RF antenna configured to transmit an RF signal forward through the LCD panel to impinge on tissue of a human user, and the at least one RF antenna comprises a receive antenna configured to receive a reflected RF signal that comprises a reflection of the RF signal impinged on tissue of the human user. The at least one processor is configured to process the reflected RF signal to generate a processed signal indicative of presence or absence of the human user, and, responsive to the processed signal, control an operating mode of the electronic device or enable control by the human user of the electronic device.

Before the foregoing subject matter is described in more detail, reflectometric detection and Doppler radar detection will be introduced.

Doppler radar utilizes the theory that a reflected radar wave off a moving target will affect the frequency of the return signal. A radar wave reflected off a target moving in a periodic forward/backward motion will exhibit a phase shift relative to the periodic motion. This periodic motion is exhibited by the human body in the form of respiration and heartbeat.

Figure 1:
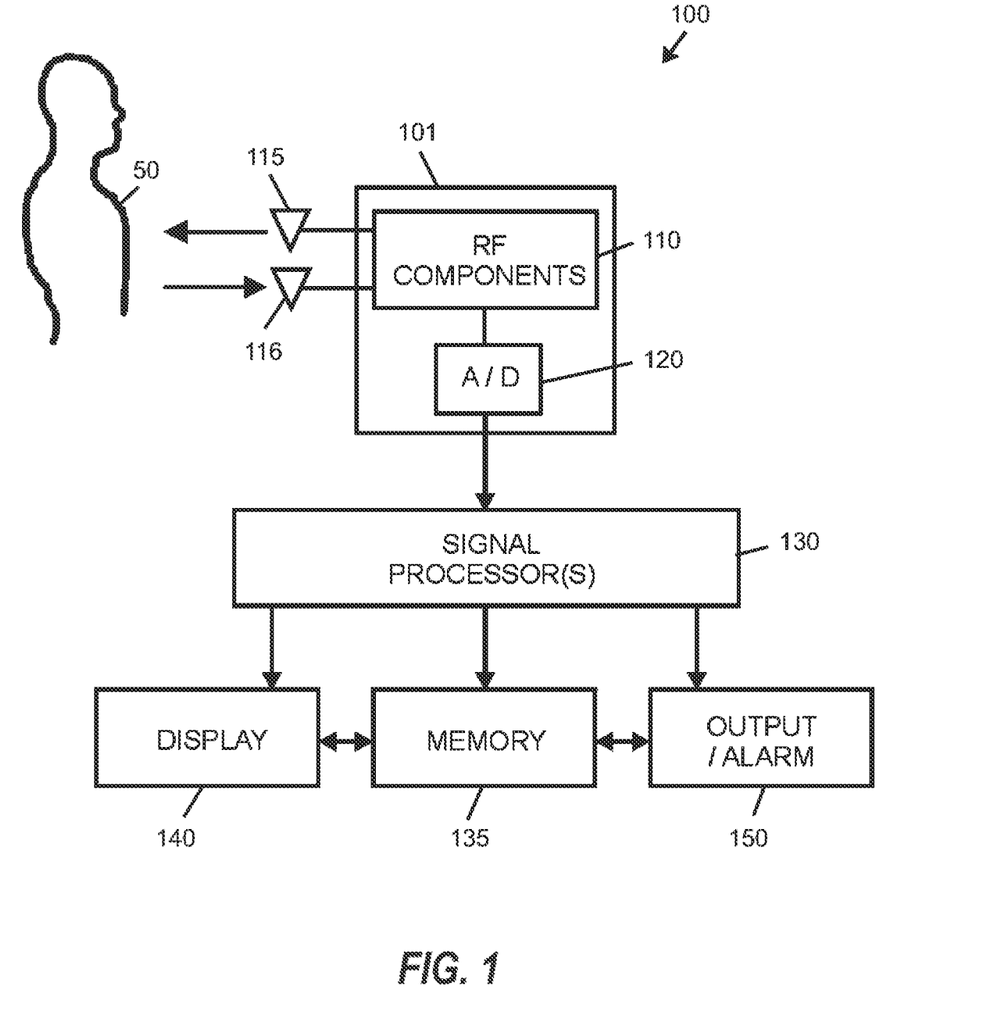
FIG. 1 is a schematic diagram illustrating connections between various components of a system for remotely sensing physiologic activity of an animal subject.
Figure 2:
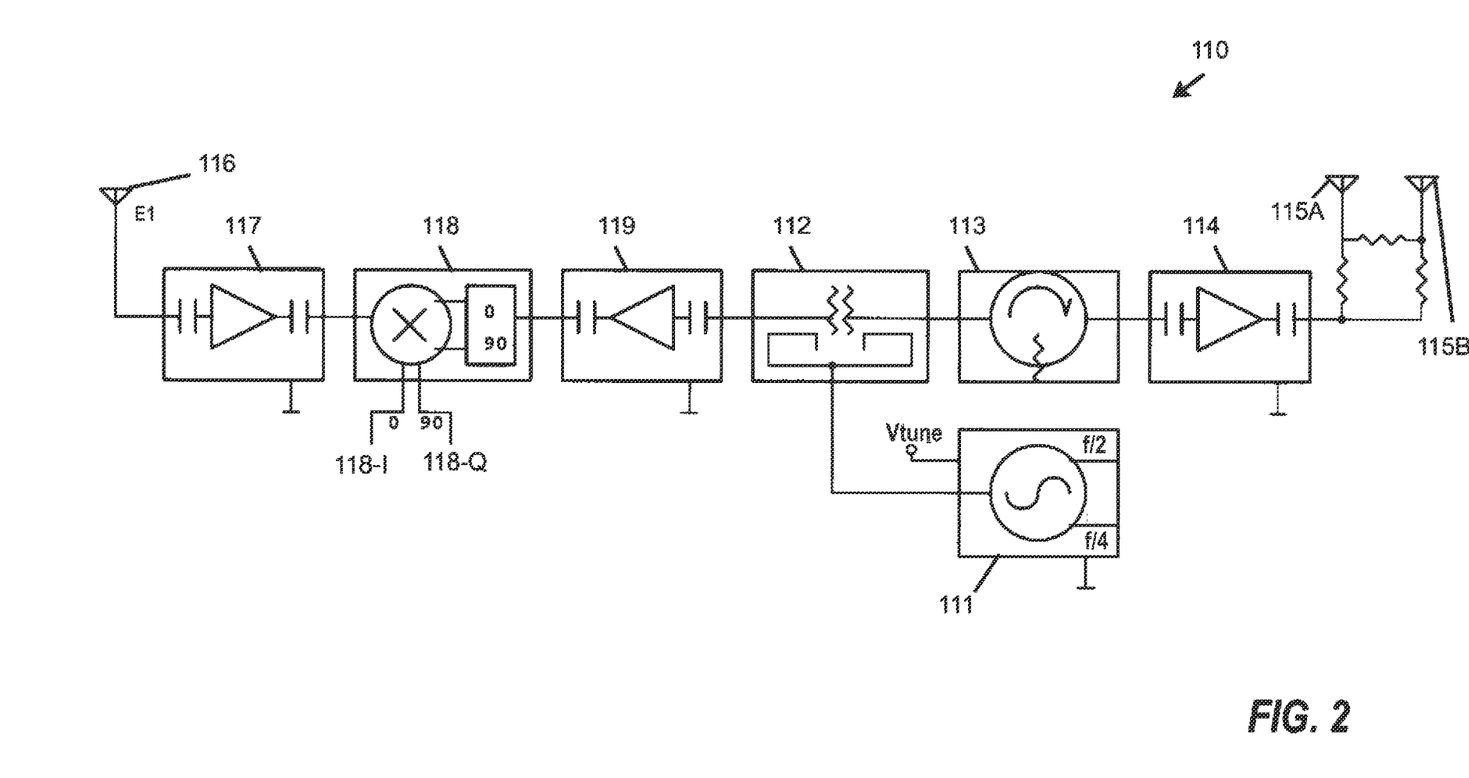
FIG. 2 illustrates connections between various radio frequency (RF) components according to one implementation of the system of FIG. 1.

Systems and methods for remotely sensing cardiac-related data of subjects have been disclosed in U.S. Pat. Nos. 9,492,099; 7,811,234; and 7,272,431. 7,811,234 discloses a non-imaging method of remotely sensing cardiac-related data of a subject, the method including: transmitting a microwave signal to illuminate tissue of the subject; receiving a reflected microwave signal, the reflected microwave signal being a reflection of the microwave signal from illuminated tissue of the subject; processing the reflected microwave signal and analyzing an amplitude of the reflected microwave signal to determine changes in a reflection coefficient at an air-tissue interface of the subject's body resulting from changes in permittivity of the illuminated tissue of the subject, the changes in permittivity containing a static component and a time-varying component; and processing the time-varying component to provide cardiographic related data of the subject. U.S. Pat. No. 9,492,099 discloses systems and methods for remote sensing of physiologic activity, including cardiac activity and respiration rate, with signal processing schemes to provide improved reproducibility despite variation in relative position between RF components and a human subject, movement of a human subject, and/or presence of interfering signals. In certain embodiments, hardware and/or filtering schemes of U.S. Pat. No. 9,492,099 may be used in implementations of systems and methods disclosed herein. The accompanying FIGS. 1 and 2 are reproduced from U.S. Pat. No. 9,492,099 to provide a further introduction to reflectometric detection of physiologic activity.

FIG. 1 illustrates connections between various components of a system 100 for remotely sensing physiologic activity (e.g., heart rate) of an animal subject 50. At least one RF transmitter 115 and at least one RF receiver 116 are arranged in sufficient proximity to the subject 50 to enable a RF signal from the RF transmitter 115 to impinge on tissue of the subject 50, and to permit a reflection of the transmitted RF signal to be received by the RF receiver 116. Multiple RF transmitters and/or RF receivers may be used, such as may be useful to mitigate motion artifacts and/or detect multiple subjects in a sensing area. Although the RF transmitter 115 and RF receiver 116 are illustrated as being spatially separated, such components may be grouped or otherwise packaged in a single component (e.g., transceiver) or assembly. The RF transmitter 115 and RF receiver 116 are arranged in communication with RF components 110 (as described in further detail in FIG. 2) to facilitate transmission and detection of RF signals. A RF signal generated by the RF transmitter 115 may include a continuous wave signal, and is preferably a microwave signal (e.g., preferably in an unregulated RF band as 900 MHz, 2.4 GHz, 5.8 GHz, or 10 GHz). The invention is not limited to use of continuous wave signals, since pulsed signals and/or other signals used in conventional radar (including Doppler radar) systems may be used, as will be apparent to one skilled in the art. An analog signal received from the RF receiver 116 is preferably converted to a baseband signal via the RF components 110 and then converted to a digital signal via at least one analog-to-digital converter 120. The RF components 110 and analog-to-digital converter 120 may be arranged on or in a single substrate and/or enclosure 101. Although preferred embodiments include use of at least one analog-to-digital converter 120, it is to be appreciated that the invention is not so limited, since one skilled in the art would appreciate that analog signals may be used and processed according to various methods disclosed herein without requiring digital conversion.

One or more signal processing components 130 are arranged to receive signals from the RF components 110 or signals derived therefrom. If signals generated by the RF components are not subject to analog-to-digital conversion, then the signal processing component(s) may include elements suitable for analog signal manipulation, such as capacitors, resistors, inductors, and transistors. In embodiments where signals from the RF components 110 are subjected to analog-to-digital conversion, the signal processing components 130 preferably embody at least one digital signal processor (processing component), such as a general purpose or special purpose microprocessor. Various functions that may be performed by one or more digital signal processors include filtering, zero-crossing detection, auto-correlation, periodicity determination, and rate computation. At least one memory element 135 is preferably arranged in communication with the one or more signal processing components 130. Additionally, at least one output and/or alarm element 150, and/or a display 140, may be arranged in communication with at least one of the signal processing components 130 and/or the memory element(s) 135. Any of various components or systems (not shown) may be connected to the output/alarm element 150, such as a control system, a communications interface, and/or other functional components.

FIG. 2 illustrates various RF components 110 according to one implementation of the system 100 described in connection with FIG. 1. An oscillator 111 is arranged to generate an oscillating wave signal at a desired frequency (e.g., 10 GHz). A splitter 112 divides the oscillating wave signal for use by the transmitting and receiving components. A circulator 113 is arranged to promote one-way flow (e.g., to the right) of a first split component of the oscillating wave signal toward a RF transmission signal amplifier 114 while attenuating any signals (e.g., noise) traveling in the opposing direction (e.g., to the left, toward the splitter 112). An amplified oscillating wave signal generated by the amplifier 114 is provided to one or more multiple RF transmitting antennas 115A, 115B, of a type (e.g., microwave) appropriate to the frequency generated by the oscillator 111.

A RF receiving antenna 116 is arranged to receive a reflected RF signal that includes a reflection of the RF signal transmitted by the transmitting antennas 115A, 115B and reflected from tissue of an animal subject. The RF signal received by the receiving antenna 116 is amplified by an amplifier 117 and then supplied to a quadrature mixer 118 that serves to mix at least a portion of a "transmitted" RF signal with the amplified received RF signal. The quadrature mixer 118 receives a split portion of the oscillating wave signal following passage through the splitter 112 and amplification by another amplifier 119. In one embodiment, the reflected radio frequency signal comprises a real signal component (I) and an out-of-phase signal component (Q), wherein the quadrature mixer 118 is arranged to generate a baseband signal (or baseband data) that includes the real signal component (I) (via output line 118-I) and the out-of-phase signal component (Q) (via output line 118-Q). In another embodiment (according to an operating mode termed QLOCK™, which is a trademark of PROBE Science, Inc., Pasadena, Calif.), the out-of-phase signal component (Q) may be kept constant (e.g., by feeding voltage from an out of phase component (Q) back to a tuned voltage of the frequency channel (e.g., via input "Vtune" associated with the oscillator 111)), and in such embodiment the quadrature mixer 118 may be arranged to output a baseband signal including only the real signal component (I). In certain embodiments, the RF components may be arranged to transmit an encoded signal to permit selective identification at the receiving end of signals received from the transmitter, thereby facilitating identification and removal of interfering signals. Encoded signal transmission may be used in conjunction with either continuous wave or pulsed signal embodiments.

With the preceding introduction to reflectometric detection being completed, aspects and embodiments of the present disclosure will now be described in further detail.

Certain embodiments disclosed herein utilize an RF transceiver, antenna(s), an analog front end, an analog/digital converter, and a processor to transmit a RF signal and receive a reflected RF signal (i.e., reflected by a human being) in order to detect the presence of a human being, utilizing the Doppler radar principle. A combination of a hardware circuit and a software algorithm may be used to extract features from the reflected RF signal in order to detect the presence of a human being. By detecting motion, respiration, and/or heart rate via signal processing of the reflected RF signal, the algorithm can accurately detect presence. Presence detection logic then feeds into the power management features of an electronic device in order to trigger power management states including sleep states.

Presence detection systems disclosed herein overcome limitations of current timer-based systems that use inactivity timers to determine when to initiate and terminate low-power operating states. Instead, presence indication as disclosed herein saves power consumption by turning off faster, and conserves work efficiency by turning on when the human being enters an operational field of view.

Figure 3:
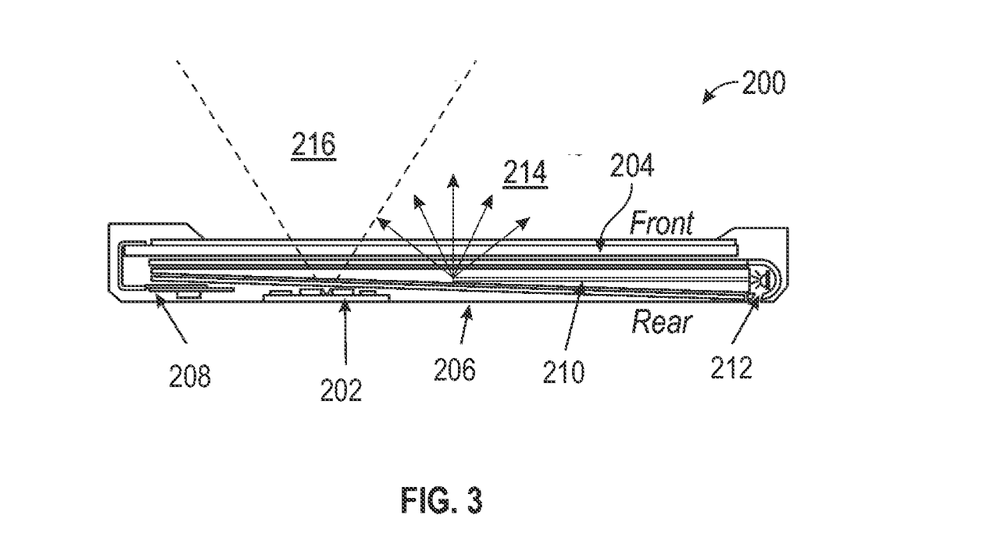
FIG. 3 is a cross-sectional view of at least a portion of an electronic device (e.g., a laptop computer) in which a radio frequency transceiver and associated circuitry are arranged behind an LCD panel, and are configured to transmit RF signals and receive reflected RF signals through the LCD panel.

FIG. 3 is a cross-sectional view of at least a portion of an electronic device 200 (e.g., a laptop computer) in which a radio frequency transceiver and associated circuitry 202 are arranged behind a LCD panel 204, and are configured to transmit RF signals and receive reflected RF signals through the LCD panel 204. The RF transmitter is directional in character, configured to transmit RF signals forwardly through the LCD panel 204. The LCD panel 204 is located forwardly of a panel casing 206, with the RF transceiver and circuitry 202 being arranged between the panel casing 206 and the LCD panel 204. The LCD panel 204 is controlled by LCD driver circuitry 208, and is illuminated by a backlight that includes a light guide (e.g., waveguide) 210 and a light source 212 (e.g., LED strip or cold cathode fluorescent device (CCFL)). Light emissions from the waveguide 210 are projected forward to illuminate the LCD panel 204, causing light emissions 214 to exit a front of the electronic device 200. Simultaneously, RF signal emissions 216 of the RF transceiver 202 are transmitted forward through the LCD panel 204 to exit a front of the electronic device 200. A field of view of the RF signal emissions may be tailored to encompass a human user when using the electronic device 200.

Figure 4:
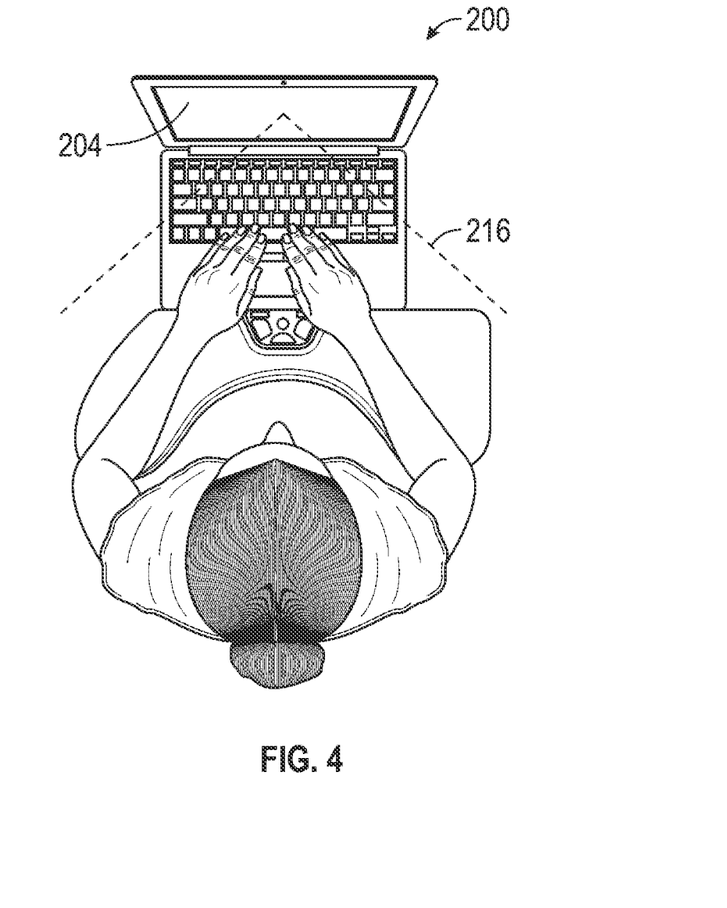
FIG. 4 is an upper perspective view illustration of a human user positioned before an LCD panel of electronic device, within the field of view of RF signal emissions emanating from a RF transmitter positioned behind the LCD panel.

FIG. 4 illustrates a human user positioned before a LCD panel 204 of an electronic device 200 (i.e., a laptop computer), within the field of view of RF signal emissions 216 (shown as dashed lines) emanating from a RF transmitter positioned behind the LCD panel 204.

Figure 5:
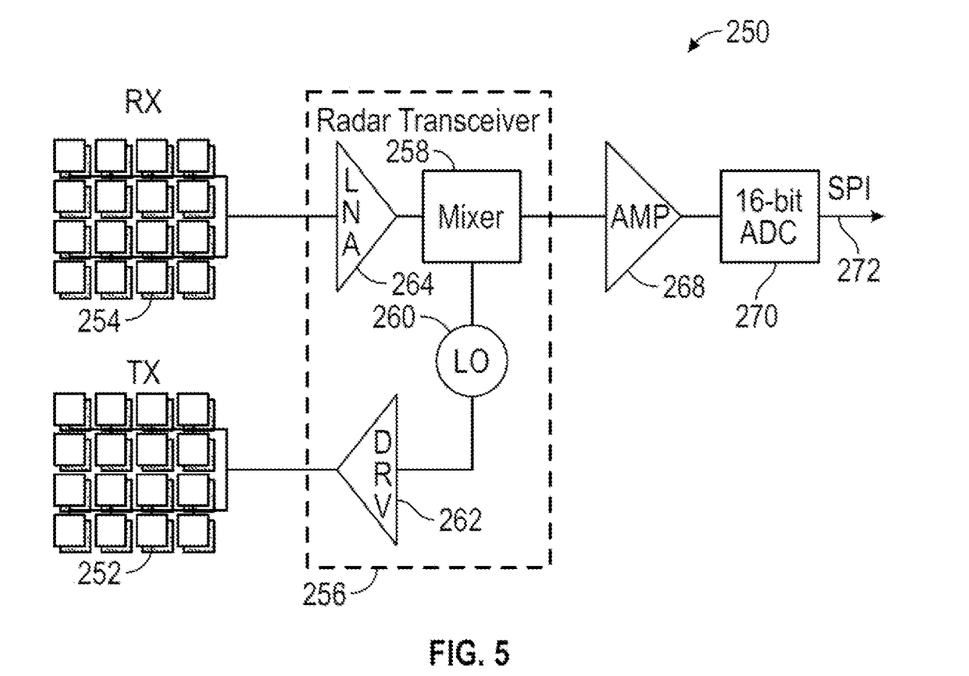
FIG. 5 is a schematic showing components of an RE radar transceiver apparatus useable with embodiments of the present disclosure.

FIG. 5 is a schematic showing components of a RF radar transceiver apparatus useable with embodiments of the present disclosure. The RF radar transceiver apparatus 250 includes a RF transmit antenna 252 and a RF receive antenna 254 coupled with radar transceiver circuitry 256. The radar transceiver circuitry 256 includes a mixer 258, a local oscillator 260, and a RF antenna driver 262 configured to drive the transmit antenna 252. The radar transceiver circuitry 256 further includes a low noise amplifier 264 configured to receive signals from the RF receive antenna 254 and pass such signals to a mixer 258 that is coupled with the local oscillator 260. Signals are thereafter amplified by a second amplifier 268 and digitally converted by an analog to digital converter 270 and sent via a serial peripheral interface (SPI) 272 to at least one downstream processor for processing as disclosed herein.

In certain embodiments, the RF transmit antenna 252 may include multiple antennas and/or the RF receive antenna 254 may include multiple antennas, providing a phased array. In certain embodiments, phase may be dynamically adjusted between multiple antennas to cause a focus of the antennas to sweep across a field of view (in a manner similar to MIMO technology for WiFi/LTE transmission). Such scheme may enable more gain and a narrower field of view, with the narrow field of view enabling reduction of antenna size and/or tracking of multiple individuals in a given field of view.

Figure 6:
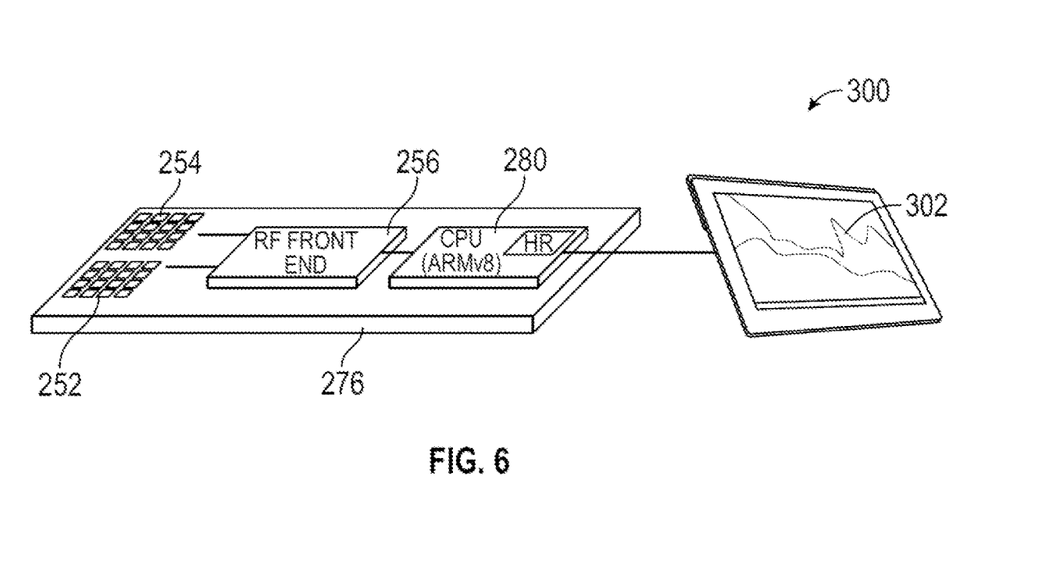
FIG. 6 is a schematic showing the RF transmit antenna, RF receive antenna. and radar transceiver circuitry of FIG. 5 together with a processor, all mounted on a circuit board and being associated with an electronic device.

FIG. 6 is a schematic showing the RF transmit antenna 252, RF receive antenna 254, and radar transceiver circuitry 256 of FIG. 5 together with a processor 280 (e.g., ARM v8 CPU) all mounted on a circuit board 276 and associated with an electronic device 300. As will be understood from the preceding disclosure, at least the RF transmit antenna 252 and RF receive antenna 254 are desirably placed behind a LCD panel 302 of the electronic device 300. As will be recognized by one skilled in the art, any suitable type(s) and/or number of processors configured to implement machine-readable instructions (e.g., software and/or firmware) may be used. In certain embodiments, a memory associated with the processor(s) is used to store machine-readable instructions to be implemented by the processor(s).

In certain embodiments, a directional transmit patch antenna may be fabricated as copper on a controlled impedance printed circuit board. The patch antenna may be designed for a particular field of view that is appropriate to cover the area (width and distance) of interest in front of the display unit, and will vary based upon the configuration of an electronic device incorporating the display. The receive antenna may be a separate instance of the same or different field of view in the case of a continuous wave (CW) RF signal. According to certain embodiments utilizing pulsed radar, a single antenna can act as the transmit and receive antenna. The transmit antenna may be fed via 50-ohm matched transmission lines to an RF transceiver. On the transmit side, the transceiver may generate a frequency specific carrier at the designed frequency operational point from a local oscillator. This frequency may be static in the case of CW, or may be chirped in the case of FM-CW. This transmit signal may be passed through the transmit antenna, and propagates through free space and any obstructions until it hits a surface that reflects the signal. The reflected signal will be modulated by the motion of the object. Free space path loss and other obstructions will attenuate the signal as a function of the square of the distance in each direction. A small portion of the reflected signal further reduced by the radar cross section of the being, hits the effective aperture of the RF receive antenna and will pass through a 50-ohm matched transmission line to the receive input of the RF transceiver. The transceiver will heterodyne the received signal with the local oscillator, and output the baseband in phase and quadrature components of the received signal. This signal contains the modulation present as a result of the properties of the reflected object in addition to a phase shift based on distance, and a coherent and non-coherent phase noise component.

These quadrature outputs will be sent to an analog front for amplification. The reflected baseband signal may be severely attenuated due to free space path loss, LCD screen materials, and low radar cross section of a human body. Such signal may be too low to be detected natively. The analog amplification may be accomplished utilizing low noise amplifiers. An analog gain of between 50× and 1000× is used to cover the ranges of interest for a presence detect system. The signal is then passed to a 16-bit analog-to-digital converter (ADC) and sampled at a rate of at least 1ksps. The ADC stores the 16-bit samples of the in-phase and quadrature components. A processor with supporting firmware reads these samples from the registers of the ADC, when the ADC signals data is available via its interrupt signal. The data samples may then then passed onto an algorithm engine which processes the data for presence information.

Once in the algorithm engine on a processor, the data samples may be vector processed for their content. The post processed samples are filtered to remove out of band noise, phase noise components as well as compensate for the phase delay based on the distance to the target object. The samples are then passed to an algorithm that detects gross motion. Gross motion is determined by fast large variations in the signal amplitude indicated by the first derivative of the post processed signal. Motion is categorized into multipole states based on thresholds that indicate the relative amount of motion being observed.

Separately, the data samples are analyzed to extract the phase modulation that corresponds to the respiration and heart rate related movement of the reflected body. The algorithm can determine the respiration rate in breaths per minute by analyzing the phase shift versus time, separating them from heart rate signals through artificial intelligence processing.

As noted previously, the location of the RF receiver (or sensor) may be behind a LCD panel so as not to interfere with the visual capabilities of the LCD display. The RF signal may be transmitted through the screen to achieve the field of view necessary for the application. At the least the RF antennas may be placed behind the LCD panel, while other components (e.g., processor circuitry) may be located elsewhere. The LCD screen attenuates the signal, and introduces a noise source on the reflected signal that must be dynamically filtered out by the algorithm. This noise source varies based on the display type and may result at least in part from active TFT array switching in the LCD panel. The filter in the algorithm may identify its location, and then remove it via digital filtering. Receiver analog amplification may be used via the op amp gain stages to provide sufficient power to overcome the attenuation provided by the LCD screen.

In certain embodiments, a presence detect algorithm works with three algorithm engines: motion, respiration and heart rate. The system is first calibrated for background noise to determine the noise floor of the environment, and indicates to the algorithm the signal characteristics when no presence is detected. It is also calibrated due to the attenuation effects of the path between the transmit antenna and the object of interest. When the gross motion algorithm identifies a large motion in the field of view of the sensor, it indicates that a presence has been detected and has presumably moved to interact with the computer system. This gross motion signal may be used as an indication for the system to exit low power mode and resume operation. Once the motion indication goes away, the respiration engine is consulted to determine if any breathing is present. This also indicates presence, and persists when the motion engine no longer sees gross motion as the person is largely still now. The system will stay in active mode as long as the respiration signal is detected, and the range is within the known operational limits of the beings of interest. Once the respiration signal is lost, the being has moved out of the view of the sensor, and the system can immediately go into a low power mode by turning off certain hardware components such as the display. In certain embodiments, the foregoing three algorithm engines may be supplemented with a blood pressure algorithm engine. In certain embodiments, a blood pressure algorithm engine may be substituted for one or more of the respiration or heart rate engines.

Figure 7A:
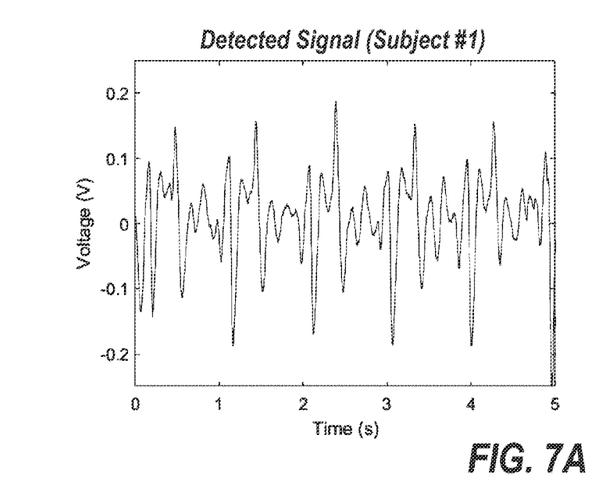
FIGS. 7A and 7B provide plots of voltage versus time for detected (raw) and post-processed signals, respectively for a first human subject.
Figure 7B:
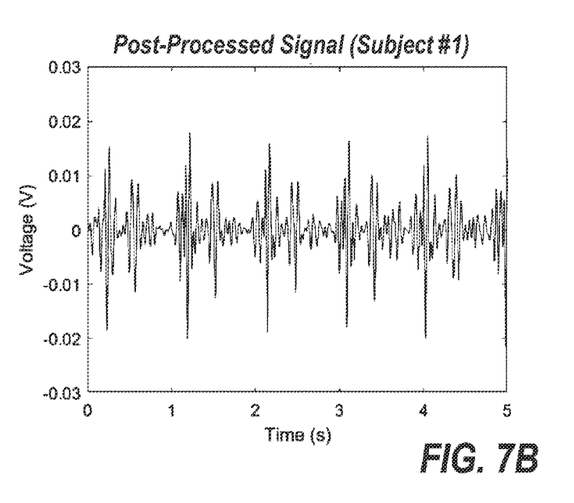
Figure 8A:
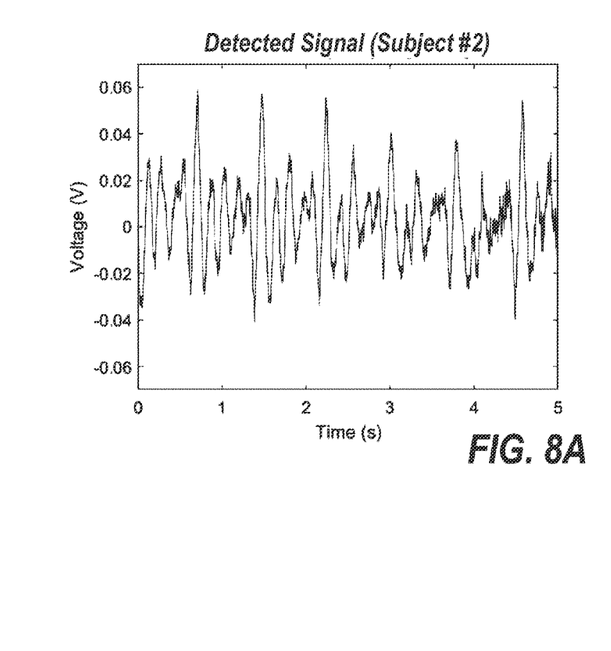
FIGS. 8A and 8B provide plots of voltage versus time for detected (raw) and post-processed signals, respectively, for a second human subject.
Figure 8B:
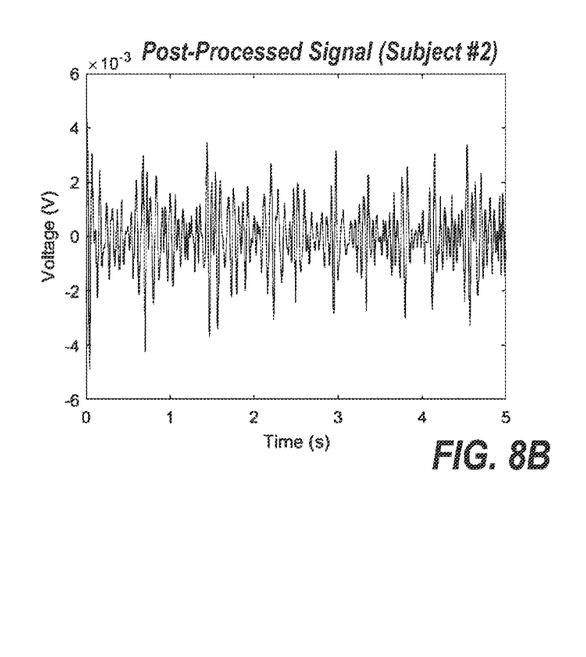

In certain embodiments, cardiac information detected by a reflected RF signal disclosed herein may include a cardiac signal signature unique to a user, and such cardiac signal signature may be compared to at least one previously stored cardiac signal signature to authenticate a human user. In response to such authentication, at least one processor may enable control of the electronic device by the authenticated user when such user is present. FIGS. 7A and 7B provide detected (raw) and post-processed signals, respectively, for a first human subject, with FIG. 7B providing a first cardiac signal signature. FIGS. 8A and 8B provide detected (raw) and post-processed signals, respectively, for a second human subject, with FIG. 8B providing a second cardiac signal signature. The first and second cardiac signal signatures may be used to identify the first and second users, respectively, and selectively permit one or both of the users to access an electronic device as disclosed herein. In certain embodiments, processing of the raw signals to obtain the post-processed signals may include: filtering the information in the time domain to isolate the unique value of the signal; transforming this information into a time-invariant domain for further processing; and extracting the cardiac signature (feature detection) using AI (Artificial Intelligence) and neural network based learning systems. In certain embodiments, the cardiac signal signature may include one or more of heart rate, temporal variations in heart rate frequency, temporal variations in signal amplitude of a cardiac signal, ratio of local peaks and/or troughs of a cardiac signal, or the like.

While the invention has been has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Various combinations and sub-combinations of the structures described herein are contemplated and will be apparent to a skilled person having knowledge of this disclosure. Any of the various features and elements as disclosed herein may be combined with one or more other disclosed features and elements unless indicated to the contrary herein. Correspondingly, the invention as hereinafter claimed is intended to be broadly construed and interpreted, as including all such variations, modifications and alternative embodiments, within its scope and including equivalents of the claims.

What is claimed is:

1. An electronic device comprising a liquid crystal display (LCD) screen, the electronic device comprising:

at least one radio frequency (RF) antenna mounted behind a LCD panel of the LCD screen, wherein the at least one RF antenna comprises a directional transmit RF antenna configured to transmit an RF signal forward through the LCD panel to impinge on tissue of a human user, and the at least one RF antenna comprises a receive antenna configured to receive a reflected RF signal that comprises a reflection of the RF signal impinged on tissue of the human user; and at least one processor configured to process the reflected RF signal to generate a processed signal indicative of presence or absence of the human user, and, responsive to the processed signal, control an operating mode of the electronic device or enable control by the human user of the electronic device;

wherein the electronic device comprises at least one of the following features (A) to (D):

(A) the processing of the reflected RF signal comprises at least one of: (i) detection of gross motion of the human user as an indicator of presence of the human user, (ii) detection of respiration rate of the human user as an indicator of presence of the human user, and (iii) detection of a cardiac signal of the human user as an indicator of presence of the human user;

(B) the at least one processor is configured to dynamically adjust sensitivity in the processing of the reflected RF signal to account for attenuation of the reflected RF signal attributable to transmission losses through the LCD panel and path loss to the human user;

(C) the at least one processor is configured to control an operating mode of the electronic device by at least one of (1) initiating a low power consumption mode or shutdown responsive to the processed signal when the processed signal indicates absence of the human user, and (2) initiating a normal power consumption mode or activation of the electronic device responsive to the processed signal when the processed signal indicates presence of the human user; and (D) the processing of the reflected RF signal comprises identifying a cardiac signal signature of the human user, and comparing the identified cardiac signal signature to at least one previously stored cardiac signal signature to authenticate the human user, to generate the processed signal indicative of presence or absence of the human user.

2. The electronic device of claim 1, wherein the RF signal comprises a pulsed RF signal.

3. The electronic device of claim 1, wherein the RF signal comprises a swept frequency RF signal.

4. The electronic device of claim 1, wherein the RF signal comprises a static RF signal.

5. The electronic device of claim 1, wherein functionality of the receive antenna is provided by the directional transmit RF antenna.

6. The electronic device of claim 1, wherein the at least one RF antenna comprises an RF antenna array.

7. The electronic device of claim 1, wherein the directional transmit RF antenna comprises a first RF antenna array, and the receive antenna comprises a second RF antenna array.

8. The electronic device of claim 1, wherein the RF signal is in a microwave frequency band.

9. The electronic device of claim 1, wherein the processing of the reflected RF signal comprises detection of gross motion of the human user as an indicator of presence of the human user.

10. The electronic device of claim 1, wherein the processing of the reflected RF signal comprises detection of respiration rate of the human user as an indicator of presence of the human user.

11. The electronic device of claim 1, wherein the processing of the reflected RF signal comprises detection of a cardiac signal of the human user as an indicator of presence of the human user.

12. The electronic device of claim 1, wherein the at least one processor is configured to dynamically adjust sensitivity in the processing of the reflected RF signal to account for attenuation of the reflected RF signal attributable to transmission losses through the LCD panel and path loss to the human user.

13. The electronic device of claim 1, wherein the at least one processor is configured to control an operating mode of the electronic device by initiating a low power consumption mode or shutdown responsive to the processed signal when the processed signal indicates absence of the human user.

14. The electronic device of claim 1, wherein the at least one processor is configured to control an operating mode of the electronic device by initiating a normal power consumption mode or activation of the electronic device responsive to the processed signal when the processed signal indicates presence of the human user.

15. The electronic device of claim 1, wherein:
the processing of the reflected RF signal comprises identifying a cardiac signal signature of the human user, and comparing the identified cardiac signal signature to at least one previously stored cardiac signal signature to authenticate the human user; and
wherein at least one processor is configured to enable control by the human user of the electronic device when the processed signal indicates presence of the human user and the human user is authenticated, to generate the processed signal indicative of presence or absence of the human user.

16. The electronic device of claim 1, embodied in a personal computer, laptop computer, or tablet computer.

17. The electronic device of claim 1, embodied in medical or industrial equipment.

18. An electronic device, comprising a liquid crystal display (LCD) screen, the electronic device comprising:
at least one radio frequency (RF) antenna mounted behind a LCD panel of the LCD screen, wherein the at least one RF antenna comprises a directional transmit RF antenna configured to transmit an RF signal forward through the LCD panel to impinge on tissue of a human user, and the at least one RF antenna comprises a receive antenna configured to receive a reflected RF signal that comprises a reflection of the RF signal impinged on tissue of the human user; and
at least one processor configured to process the reflected RF signal to generate a processed signal indicative of presence or absence of the human user, and, responsive to the processed signal, control an operating mode of the electronic device or enable control by the human user of the electronic device;
wherein the processing of the reflected RF signal comprises detection of respiration rate, blood pressure, and/or a cardiac signal, without identification of gross motion of the human user, as an indicator of presence of the human user.

19. The electronic device of claim 18, wherein the RF signal comprises one of: a pulsed RF signal, a swept RF signal, or a static RF signal.

20. The electronic device of claim 18, embodied in a personal computer, a laptop computer, a tablet computer, medical equipment, or industrial equipment.

\* \* \* \* \*